(12) United States Patent
Cubicciotti

(10) Patent No.: US 7,005,132 B2
(45) Date of Patent: Feb. 28, 2006

(54) PRODRUG COMPOSITIONS AND DRUG DELIVERY METHODS USING SYNTHETIC RECEPTORS

(75) Inventor: Roger S. Cubicciotti, Montclair, NJ (US)

(73) Assignee: Molecular Machines, Inc., Montclair, NJ (US)

( * ) Notice: Subject to any disclaimer, the term of this patent is extended or adjusted under 35 U.S.C. 154(b) by 514 days.

(21) Appl. No.: 09/171,885

(22) PCT Filed: May 2, 1997

(86) PCT No.: PCT/US97/07491

§ 371 (c)(1),
(2), (4) Date: Oct. 28, 1998

(87) PCT Pub. No.: WO97/41840

PCT Pub. Date: Nov. 13, 1997

(65) Prior Publication Data

US 2002/0122810 A1    Sep. 5, 2002

Related U.S. Application Data

(60) Provisional application No. 60/016,566, filed on May 3, 1996.

(51) Int. Cl.
*A61K 9/00* (2006.01)
(52) U.S. Cl. ................. 424/400; 424/450; 424/175.1; 436/829
(58) Field of Classification Search ............... 424/450, 424/400, 175.1; 436/829
See application file for complete search history.

(56) References Cited

U.S. PATENT DOCUMENTS 5,028,535 A    7/1991  Buechler et al. ............. 435/7.1
5,106,951 A *  4/1992  Morgan, Jr. et al. ..... 530/391.9
5,252,713 A * 10/1993  Morgan, Jr. et al. ..... 530/391.7

OTHER PUBLICATIONS

Betageri GV, et al., (1994), "Liposomes as drug carriers", Pharmaceutical Engineering 14:8-16.
Hinds, JA, et al., (1984), "Ligand displacement immunoassay: a novel enzyme immunoassay demonstrated for measuring theophylline in serum", Clinical Chemistry 30: 1174-1178.
Kaufman S. (1994), "Random chemistry", Ber. Bunsenges. Phys. Chem. 98:1142-1147.
Kenan DJ, et al., (1994), "Exploring molecular diversity with combinatorial shape libraries", TIBS 19:57-64.
Matsui K., et al., (1991), "Low affinity interaction of peptide-MHC complexes with T cell receptors", Science 254:1788-1791.
O'Connell J.P., et al., (1985), "A highly sensitive immunoassay system involving antibody-coated tubes and liposome-entrapped dye", Clinical Chemistry 31:1424-1426.
Ostresh JM, et al., (1994), "'Libraries from libraries': Chemical transformation of combinatorial libraries to extend the range and repertoire of chemical diversity", Proc. Natl. Acad. Sci. USA 91:11138-11142.
Szabo G, et al., (1989), "Fluorescent staphylococci as microbeads", Cytometry 10:801-802.

* cited by examiner

*Primary Examiner*—Thurman K. Page
*Assistant Examiner*—Lakshmi Channavajjala
(74) *Attorney, Agent, or Firm*—Kathleen A. Tyrrell

(57) ABSTRACT

The present invention provides prodrug and multiprodrug complexes comprising drugs specifically bound to synthetic receptors in such a manner that active drug becomes available only in the presence of a targeted pathophysiologic receptor. Methods for preparation end use of these prodrug complexes in drug delivery systems are also provided.

7 Claims, No Drawings

PRODRUG COMPOSITIONS AND DRUG DELIVERY METHODS USING SYNTHETIC RECEPTORS

This application claims the benefit of 60/016,566 filed May 3, 1996.

INTRODUCTION

This application is related to Disclosure Document No. 353687, received May 6, 1994 entitled "Smart drugs: prodrug compositions and drug delivery methods using synthetic receptors".

BACKGROUND OF THE INVENTION

Research in drug delivery technology continues to escalate as innovative delivery systems are found in many cases to offer advantages over conventional drug formulations. For example, alternate drug delivery systems have been shown to provide therapeutic advantages by increasing efficacy and safety, while reducing side effects. Many of these systems offer usage benefits to the patient, including more convenient dosage forms and administration schedules. In addition, alternate delivery systems enable new indications for approved drugs, including generics. Further, the development of new drug delivery systems has expedited approval and widespread use of many new drugs in development. Accordingly, the worldwide market for alternate drug delivery systems has more than doubled over the past five years to approximately $6 billion, and annual growth rates averaging 30% to 40% have been projected for the next several years. Examples of FDA-approved drug delivery systems include polymers, osmotics, liposomes, nasal and transdermal formulations, aerosols and resins. Emerging delivery systems include gels, foams, microparticles, red blood cells and prodrugs. In addition, many device technologies are being developed to improve the efficiency and/or convenience of drug administration, including controlled infusion devices (e.g., for patient-controlled analgesia), metered-dose inhalers and implantable pumps.

Alternative drug delivery systems are particularly important for emerging biopharmaceuticals, which represent the most active area of therapeutic market growth and product innovation. The vast majority of approved and pending biopharmaceuticals are recombinant peptides and proteins that cannot be efficiently administered orally and may be either ineffective, preclusively inconvenient or otherwise unacceptable as injectibles. The commercial potential of such compounds and the rate of market development will depend in large part on improved drug delivery systems.

Drug delivery systems are defined herein as dosage forms (comprising one or more drugs) that provide increased control over drug concentration and/or duration of action either systemically or at anatomically or pathophysiologically defined sites. Primary approaches being developed include controlled release formulations, local delivery of drugs in biocompatible matrices, targeted delivery using receptor- or membrane-directed agents and prodrug compositions that remain therapeutically inactive until converted to active drug in vivo.

Local delivery is intended to provide a therapeutically effective concentration of drug at the desired site of action for a clinically appropriate period of time without the toxicity and side effects that might result from systemic administration. Representative indications include periodontal diseases, ophthalmic infections and a variety of cancers. Approaches in development include bioerodable polymers, gels, foams, microparticles, microvesicles, proteinaceous matrices and implantable pumps. Most local delivery approaches include a built-in sustained release mechanism to provide prolonged action following administration. However, local delivery requires convenient access to the site of interest, preferably either by noninvasive techniques or an otherwise-indicated surgical procedure. Further, local delivery fails to provide diffuse or systemic protection, as may be important in metastatic disease, fulminant infections or other conditions prone to migration from a primary site.

Controlled release formulations are designed to maintain drug concentrations within the therapeutic range without the dramatic peak-to-trough variability that occurs with conventional administration. Elimination of peak levels improves drug safety by reducing toxicity and side effects. Avoiding troughs obviates the risk of symptoms being unmasked during periods of subtherapeutic drug levels. Most controlled release technologies incorporate a sustained release mechanism that provides for prolonged action of drugs with short half-lives, thereby increasing dosage intervals, ease of use and patient compliance. Prodrugs represent a special category of controlled release formulations, wherein the drug composition is inactive as administered, but is converted to active form in vivo through exposure to a particular physiologic environment or metabolic process. Controlled release has been successfully used to increase the bioavailability of orally administered drugs, to minimize fluctuations in systemic drug levels, to provide coarse control over biodistribution and to increase the half-life of drugs administered both locally and systemically. A major shortcoming of controlled release formulations, however, is the limited extent to which drug disposition can be practically controlled through nonselective mechanisms.

Drug targeting refers to preferential delivery of therapeutic agents to clinically relevant organs, tissues, cells or receptors. Preferential delivery is achieved either through specific molecular targeting agents or through methods that alter the physicochemical properties of a drug so as to alter its pharmacokinetic properties and biodistribution. Specific molecular targeting agents such as monoclonal antibodies, lectins, peptides and specific sugars selectively bind to pathophysiologic receptors, thereby bringing a conjugated drug into close proximity with its site of action. Altering the physicochemical properties of a drug or drug-carrier complex can nonselectively influence drug distribution through effects on binding and uptake by different cell types and transport across physiologic barriers such as the gastric mucosa, skin, capillary membrane and blood-brain barrier. Examples of targeting approaches include immunoconjugates and monoclonal antibody-modified liposomes designed to specifically bind clinically significant receptors or disease markers and drugs conjugated to carriers or delivered in vehicles that enhance membrane permeability. However, such therapeutic conjugates have yet to be widely accepted. Aside from technical challenges related to tissue penetration, stability and immunogenicity, a problem with immunoconjugates and related targeting strategies is that they do not increase the percent of administered drug that gains access to the desired site of action. Affinity-based targeting agents increase the probability that a drug near its site of action will exert an effect, but they fail to increase the percentage of administered drug that reaches the desired site. Accordingly, these agents do not provide a mechanism to sequester or concentrate drug at the desired site of action. Affinity-based delivery vehicles in development provide only for partitioning of drug conjugates between bound (e.g., to targeted receptors) and free (e.g., in extracellular fluid) phases, which partitioning is directly dependent on the bulk concentration of drug conjugate. The efficiency of delivery is therefore limited both by the affinity of the targeting agent for its receptor and by the percentage of administered drug that distributes to therapeutically relevant sites. In general, treatment of localized conditions such as cancers, infections and vascular occlusions by systemic administration of therapeutic immunoconjugates is highly inefficient. only a small fraction (<1%) of administered conjugate interacts with targeted receptors, the remainder being metabolized and excreted.

Accordingly, there is a growing need for drug delivery systems that provide greater efficiency, safety, duration of action and convenience than current drug targeting methods.

SUMMARY OF THE INVENTION

An object of the present invention is to provide a prodrug complex comprising a drug specifically bound to a synthetic receptor, wherein the specifically bound drug becomes therapeutically active only upon dissociation from the synthetic receptor.

Another object of the present invention is to provide a prodrug complex comprising a drug specifically bound to a synthetic receptor, wherein the in vivo half-life of the prodrug complex is greater than the in vivo half-life of the drug administered in unbound form.

Another object of the present invention is to provide a prodrug complex comprising a biopharmaceutical specifically bound to a synthetic receptor, wherein the in vivo stability of the biopharmaceutical is increased when it is specifically bound to the synthetic receptor.

Another object of the present invention is to provide a multi-prodrug reservoir comprising multiple drug molecules specifically bound to a heteropolymer, wherein the drug molecules are specifically bound at a repeating synthetic receptor motif comprising a monomer sequence selected by combinatorial methods.

Another object of the present invention is to provide an immobilized prodrug complex comprising a drug specifically bound to a synthetic receptor which is operatively attached to a biologic or biocompatible structure, wherein the in vivo half-life of the immobilized prodrug complex is greater than the in vivo half-life of either the prodrug complex or the drug administered alone.

Another object of the present invention is to provide a method for modulating the transport of a drug across a biologic membrane by administering the drug in the form of a prodrug complex or immobilized prodrug complex.

Another object of the present invention is to provide a method for increasing the duration of action of an administered dose of drug by administering the drug in the form of a prodrug complex or immobilized prodrug complex.

Another object of the present invention is to provide a method for increasing the percentage of an administered dose of drug that interacts with its therapeutic receptors by administering the drug in the form of a prodrug complex or immobilized prodrug complex.

Another object of the present invention is to provide a method for reducing the physiologic concentration of drug available for nonspecific interactions following administration of a therapeutically effective dose by administering the drug as a prodrug complex or immobilized prodrug complex.

Another object of the present invention is to provide a method for regulating the rate of drug delivery in proportion to the number, concentration or activity of targeted receptors by administering the drug as a prodrug complex or immobilized prodrug complex.

Another object of the present invention is to provide a method for reducing the frequency of administration, cumulative dose, toxicity and side effects of a drug without decreasing therapeutic efficacy by administering the drug as a prodrug complex or immobilized prodrug complex.

DETAILED DESCRIPTION OF THE INVENTION

The present invention provides methods, compositions and applications for efficient, site-specific drug delivery using prodrug or multi-prodrug complexes comprising therapeutic agents specifically bound to synthetic receptors. Preferred embodiments of these complexes enhance drug delivery by providing for increased specificity, efficiency and duration of therapeutic action over conventional pharmaceutical formulations and emerging methods for drug targeting such as immunoconjugates, fusion proteins, and liposomes, and controlled drug delivery such as microparticles, bioerodable polymers, gels, and foams. In addition, binding of a selected drug to a synthetic receptor provides increased stability to the selected drug, thereby also enhancing drug delivery. These complexes comprise drugs or known chemical entities that remain substantially inactive or unavailable in the absence of a targeted pathophysiologic receptor to which they specifically bind with relatively high affinity. In the presence of such pathophysiologic receptors, drug dissociation and rebinding results in target-dependent delivery of drug from synthetic receptors to pathophysiologic receptors. Therapeutic benefits are achieved through administration of a prodrug complex or multi-prodrug complex of the present invention comprising at least one drug molecule specifically bound to at least one synthetic receptor.

For the purposes of the present invention, "drug" is meant to include any molecule, molecular complex or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure. The term "prodrug" refers to a drug, drug precursor or modified drug that is not fully active or available until converted in vivo to its therapeutically active or available form. The term "prodrug complex" refers to a prodrug comprising at least two non-covalently bound molecules and includes, without limitation, a drug specifically bound to a synthetic receptor. The term "multi-prodrug complex," also described herein as a "multi-prodrug reservoir," refers to a prodrug complex comprising at least two drug molecules specifically bound to at least two synthetic receptors. The terms "specifically bind," "specifically bound" and "specific binding" refer to saturable, noncovalent interaction between a ligand and a receptor that can be competitively inhibited by structural analogs of the ligand. The terms "dissociable" and "displaceable" refer to specifically bound ligand-receptor complexes capable of undergoing net dissociation in the presence of a second specific binding partner for either the ligand or the receptor of said ligand-receptor complexes. The term "ligand" refers to a specific binding partner of a receptor and includes, without limitation, receptor agonists, partial agonists, mixed agonists, antagonists, drugs, hormones, transmitters, autocoids, growth factors, cytokines, prosthetic groups, coenzymes, cofactors, regulatory factors, antigens, haptens, vitamins, nucleic acids and synthetic heteropolymers comprising amino acids, nucleotides, carbohydrates or nonbiologic monomers, including analogs and derivatives thereof, and conjugates or complexes formed by attaching or binding any of these molecules to a second molecule. The term "receptor" refers to a specific binding partner of a ligand and includes, without limitation, membrane receptors, soluble receptors, cloned receptors, recombinant receptors, hormone receptors, drug receptors, transmitter receptors, autocoid receptors, cytokine receptors, antibodies, antibody fragments, engineered antibodies, antibody mimics, molecular recognition units, adhesion molecules, agglutinins, integrins, selectins, nucleic acids and synthetic heteropolymers comprising amino acids, nucleotides, carbohydrates or nonbiologic monomers, including analogs and derivatives thereof, and conjugates or complexes formed by attaching or binding any of these molecules to a second molecule. The term "specific binding pair" refers to a ligand and a corresponding receptor. The term "synthetic receptor" refers to any naturally occurring, recombinant, biologically produced or synthetic ligand or receptor which is designed, selected or engineered to specifically bind a drug. The terms "therapeutic receptor" and "pathophysiologic receptor" refer to the molecular site of drug action. The term "therapeutic target" refers to an object of therapeutic intervention, including any physiologic or pathologic entity comprising therapeutic receptors, such as a specified organ, tissue or type of cell, platelet, corpuscle, microorganism, molecular complex or molecule. The term "biocompatible" refers to an exogenous substance that is nonimmunogenic, nonallergenic and nontoxic when administered in vivo.

In contrast to existing methods that rely upon either active or passive drug targeting or controlled drug delivery, including sustained release, prolonged action and repeat action formulations, the complexes of the present invention rely upon drug partitioning through differential affinity for a synthetic receptor versus the targeted pathophysiologic receptor. The present invention entails administration of drug prebound to a specific binding partner, partitioning of drug between synthetic receptors and therapeutic targets, and target-dependent availability of active drug, thereby providing for specific partitioning of a single ligand between different receptors. The invention can be further improved for certain applications by operative attachment of a synthetic receptor to a biologic or biocompatible structure to either the synthetic receptor or the drug. By operative attachment, it is meant that the synthetic receptor may be either directly attached to said structure or indirectly attached through an intermediate (e.g. a carrier, drug or spacer), and the attachment may be either covalent or noncovalent. It will be apparent to those of skill in the art that covalent attachment of a selected drug or synthetic receptor requires chemical modification, which may include introduction of new groups, modification, transformation or blocking of groups, attachment to groups, crosslinking and the like. For the purpose of this disclosure, the terms "drug" and "synthetic receptor" include drugs and synthetic receptors that have been chemically modified and/or attached to a biologic or biocompatible structure.

Synthetic receptors which are used in the prodrug and multi-prodrug complexes of the present invention can be selected and produced by a number of different methods well known to those of skill in the art including, but not limited to, monoclonal antibody technologies and combinatorial techniques for selecting heteropolymers of natural or modified amino acids, nucleotides, carbohydrates or small organic molecules from sequence and shape libraries. Screening of encoded chemical libraries, for example, has been used to identify synthetic receptors capable of binding to various large and small molecules. See, e.g., Kauffman, S. Ber. Bunsenges. Phys. Chem. 1994 98:1142–1147; Kenan et al. TIBS 1994 19:57–64; Ostresh et al. Proc. Nat'l. Acad. Sci USA 1994 91:11138–11142. The present invention applies such techniques to the selection of synthetic receptors useful in prodrug complexes that provide for improved drug delivery. Synthetic receptors are identified through iterative screening and selection for specific binding attributes and physicochemical properties, preferably from a diverse pool of molecular candidates and more preferably from a combinatorial shape library. Classes of molecules (and corresponding mimetics) from which synthetic receptors may be selected include, without limitation, antibodies and engineered antibodies, oligonucleotides, oligosaccharides, peptides, organic polymers such as polyhydroxyalkanoates, polyphenols, polyphosphates and polysulfates, and derivatives, analogs or combinations thereof. Optimization of the solubility and circulating half-life of the prodrug complex is achieved through multifactorial selection from panels of synthetic receptors differing in molecular size and net charge (e.g., degree of ionization under physiologic conditions). The pharmacologic half-life of dissociable drug is maximized by further selecting synthetic receptor candidates on the basis of relative affinity for the drug compared with the apparent affinity of the drug for isolated targeted pathophysiologic receptors.

In a preferred embodiment, the prodrug complex of the present invention may further be operatively attached to a carrier. This may be achieved by first attaching either the drug or the synthetic receptor to a carrier and then specifically binding the complementary specific binding partner. Alternatively, the drug and synthetic receptor may first be specifically bound to one another to form a prodrug complex which is then operatively attached to a carrier. The carrier may be any biologic or biocompatible molecule, molecular complex or microstructure which is cleared less rapidly than free drug, preferably a cell, vesicle, microparticle, polymer, gel or matrix and more preferably a blood forming element or reticuloendothelial cell. As will be understood by those skilled in the art, a carrier may be attached to either the drug or synthetic receptor prior to or after formation of the prodrug complex. Benefits over alternative drug delivery technologies include improved safety, efficacy and patient compliance, more convenient dosing schedules and reduced treatment costs.

Formation of quasi-stable complexes of specific binding partners that are subsequently displaced in an analyte-dependent manner has been demonstrated in immunodiagnostic products. See, e.g., U.S. Pat. No. 5,028,535; Hinds et al. Clinical Chemistry 1984 30:1174–1178; Matsui et al. Science 1991 254:1788–1791. The present invention applies quasi-stable complexes of drugs and synthetic receptors to therapeutic compositions and drug delivery methods.

Protection of biopharmaceuticals such as oligonucleotides against enzymatic degradation has been achieved by covalently attaching conjugate groups near the enzyme recognition site. Synthetic receptors of the present invention can be noncovalently bound to biopharmaceuticals at sites that occlude enzyme access. The term "biopharmaceutical" includes drugs that are either produced biologically or synthesized from carbohydrates, amino acids, lipids, nucleotides or derivatives or analogs thereof. Prodrug complexes of the present invention thereby provide a versatile method for protecting biopharmaceuticals from enzymatic degradation thus enhancing drug delivery.

Operative attachment of ligands to cells, liposomes, microparticles and other structures has been applied to both immunodiagnostic tests and drug delivery. See, e.g., O'Connell et al. *Clinical Chemistry* 1985 31:1424–1426; Szabo, G. and Damjanovich, S. *Cytometry* 1989 10:801; Betageri, G. V. and Habb, M. J. *Pharmaceutical Engineering* 1994 14:8–16. Ex vivo modification of erythrocytes and lymphocytes for subsequent diagnostic and therapeutic use has also been demonstrated, as has stabilization of liposomes for prolonged-action drug delivery. In the present invention similar techniques are applied to development of microcarrier-immobilized prodrug complexes that release active drug in proportion to the availability of therapeutic receptors, rather than passive release or delivery at a predetermined rate.

Biocompatible matrices and microparticles have been developed for therapeutic implants, prosthetic devices and controlled drug delivery. The present invention provides methods and compositions that use such biocompatible structures as carriers for controlling the distribution and half-life of novel prodrug complexes. Preferably, compositions include biopolymers and synthetic organic equivalents comprising repeating synthetic receptor motifs within heteropolymers of different size and shape that can be synthesized with defined and reproducible molecular composition. Linear, branched and cyclized biopolymers comprising nucleotides, amino acids, saccharides, fatty acids, phenols, phosphates, sulfates and/or other organic monomers arranged with repeating sequences can be preselected for specific binding to drugs of interest.

An important advantage of the present invention is the versatility which permits an array of compositional permutations from which to select and optimize specific embodiments for different clinical indications, drug classes, target distribution and pharmacokinetic objectives. For example, a first embodiment involves use of drugs in specifically bound form, wherein the selected synthetic receptor serves to minimize nonspecific binding of the drug to low affinity sites and protects against unwanted cellular uptake and metabolic degradation. Because the drug's active site is specifically bound to a synthetic receptor, the drug-partner complex is functionally inactive until drug is released to a therapeutic receptor and therefore fits the definition of a "prodrug." In this embodiment, different synthetic receptor design and selection strategies are required depending on the drug of choice, the preferred duration of drug action, and the physioanatomic distribution and microlocalization of therapeutic targets.

Using this embodiment, the safety and duration of action of a conventional pharmaceutical can be improved. For example, use of this complex with a drug for which clinical utility is limited by toxicity, side effects, inconvenient dosing and/or associated patient noncompliance can minimize peak-to-trough fluctuations, reduce adverse effects and sustain therapeutic action of a systemically administered drug. Examples of drugs for which this complex is especially suited include, but are not limited to: anti-infectives that bind to membranes of sensitive organisms such as polyene antifungals and glycopeptide antibiotics or are internalized by receptor-mediated processes such as isoniazid, aminoglycosides, and tetracyclines; allergy, asthma and ulcer drugs that act at receptors for histamine, such as terfenadine and cimetidine and other autocoids such as bradykinins, prostacyclins, serotonins, and leukotrienes; cardiovascular drugs and antihypertensives such as cardiac glycosides, ACE inhibitors, beta-blockers and calcium antagonists; antithrombotics such as thrombin inhibitors and platelet receptor antagonists. This type of prodrug complex is designed to release active drug to extracellular or external membrane receptors such that therapeutic action does not require cellular uptake. In addition, the selected synthetic receptor enhances cellular uptake of specifically bound drug relative to free drug, thereby favoring drug action on intracellular receptors.

A second embodiment, further involves operative attachment of specifically bound drug-partner complexes to blood forming elements, reticuloendothelial cells or long half-life, biocompatible microstructures (e.g., liposomes, microspheres) or nanostructures (e.g., biopolymers, multimolecular complexes). This embodiment provides a method to continuously perfuse therapeutic targets with high capacity microreservoirs of inactive prodrug complexes in such a manner that active drug dissociates in proportion to therapeutic receptor levels. The circulating half-life and biodistribution of carrier-bound prodrug complexes can be optimized for different applications by selecting carriers with different physical and chemical properties (e.g., size, shape, degree of ionization, lipid solubility).

In a preferred embodiment, preselected synthetic receptors are built into a biocompatible carrier such as a biopolymer comprising sequences of monomers (e.g., nucleotides, amino acids, saccharides, fatty acids, phenols, phosphates, sulfates) arranged as repeating synthetic receptor motifs. In this preferred embodiment, multiple drug molecules specifically bind to a biopolymer comprising multiple synthetic receptors to form a multi-prodrug complex.

Another embodiment of the present invention, involves operative localization of prodrug complexes to a given site, tissue, fluid space or cavity which is accessible either noninvasively, by injection or during endoscopy, catheterization or surgical procedures. Prodrug complexes can be attached either directly to cell membranes or to implants or biocompatible matrices deposited or injected at the site of interest. This embodiment enables sustained retention of prodrug complexes at or near a site of localized injury, infection, inflammation, disease or dysfunction with continuous dissociation of active drug in proportion to the local concentration of therapeutic targets.

The prodrug complexes of the present invention are useful in achieving therapeutically effective drug concentrations at defined targets including organs, tissues, cells, receptors or pathologic sites, safely and cost-effectively. These complexes are also useful in eliminating peak to trough fluctuations in drug levels characteristic of intermittent dosing, thereby circumventing the risk of subtherapeutic and toxic phases. In addition, by using these complexes, therapeutic levels at desired sites are sustained for clinically effective periods of time. Further, use of these complexes minimizes exposure of nonpathologic sites to therapeutic agents, thereby reducing the incidence of toxicity and side effects.

Other fields of use for the complexes of the present invention will be obvious to those of skill in the art upon this disclosure and include, but are not limited to, cosmetics, nutraceuticals, medical imaging, agriculture (e.g., pesticides, fertilizers, herbicides and agriceuticals) industrial processing (e.g., food and beverages, biologicals and biotechnology-derived products) and environmental remediation.

The following nonlimiting examples are provided to further illustrate the present invention.

EXAMPLES

Example 1

Prodrug Complex Comprising Amphotericin B

The advantages of these complexes will vary depending on the particular indication and corresponding drug of choice. For a drug such as amphotericin B, primary advantages relate to safety, solubility and duration of therapeutic action. Amphotericin B has been in clinical use for over thirty years and, despite toxicity problems, remains the drug of choice for systemic fungal infections. One of its most serious adverse effects is renal toxicity, which occurs in up to one-third of patients receiving therapeutically effective doses. Amphotericin B is insoluble in water, requiring controlled infusion of a colloidal suspension in neutral dextrose solution and precautionary monitoring of intravenous lines to ensure patency. To address toxicity and infusion problems, liposomal and/or "lipid complex" formulations of amphotericin B are being developed. Amphotericin B is believed to act by mechanically disrupting cell membranes following preferential binding to ergosterol-containing fungal plasma membranes as opposed to cholesterol-rich mammalian cell membranes. Accordingly, the prodrug complex of the present invention provides a means for increasing selectivity for fungi by specifically partitioning drug from synthetic receptors to ergosterol-containing membranes, thereby reducing toxic effects on mammalian cells. Selection of a suitably hydrophilic (ionized) synthetic receptor also provides a stable, soluble dosage form to overcome the inconvenience, cost and risk of controlled infusion.

A prodrug complex comprising amphotericin B specifically bound to a synthetic receptor comprising amino acids, nucleotides, sugars and/or other small organic monomers is formulated.

Synthetic receptors useful in this formulation are identified through iterative screening and selection for specific binding attributes and physicochemical properties, preferably from a diverse pool of molecular candidates and more preferably from a combinatorial shape library. Classes of molecules (and corresponding mimetics) from which synthetic receptors may be selected include, without limitation, antibodies and engineered antibodies, oligonucleotides, oligosaccharides, peptides, organic polymers such as polyhydroxyalkanoates, polyphenols, poylphosphates and polysulfates, and derivatives, analogs or combinations thereof. Optimization of the solubility and circulating half-life of the prodrug complex is achieved through multifactorial selection from panels of synthetic receptors differing in molecular size and net charge (e.g., degree of ionization under physiologic conditions). The pharmacologic half-life of dissociable drug is maximized by further selecting synthetic receptor candidates on the basis of relative affinity for amphotericin B compared with the apparent affinity of the drug for isolated fungal membranes.

Example 2

Prodrug Complex for Stabilizing HIV Aptamer

The in vivo half-life and efficacy of a biopharmaceutical can be improved using prodrug complexes of the present invention. Biopharmaceutical classes amenable to this embodiment include, but are not limited to, peptides (e.g., hormones, releasing factors, molecular recognition units), proteins (e.g., monoclonal antibodies, recombinant antigens, hormones, interferons, colony stimulating factors), oligonucleotides (e.g., antisense, ribozymes, aptamers), oligosaccharides (e.g., cell adhesion molecules, immunomodulators, anti-infectives) and hybrid structures such as glycopeptides and glycolipids.

For example, an aptamer that specifically binds and inhibits HIV reverse transcriptase is protected against enzymatic degradation by administration in specifically bound form. The specific binding partner of the anti-HIV aptamer may be either a synthetic receptor selected from a combinatorial shape library or an oligonucleotide that hybridizes to the aptamer through Watson-Crick base pairing with a suitable degree of complementarity to yield quasi-stable hybrids that are dissociable in the presence of HIV reverse transcriptase. These oligonucleotides are generated by in vitro evolution from initial sequence segments complementary to different nucleotide sequences of the anti-HIV aptamer. In this embodiment, at least one HIV aptamer is selected for specific binding to a relatively conserved region of HIV reverse transcriptase from a randomized pool or combinatorial shape library comprising oligonucleotides generated by in vitro evolution. Potentially useful shape libraries include, without limitation, populations of polymeric conformers prepared from random combinations of amino acids, nucleotides, carbohydrates and other organic monomers. Selected synthetic receptors are first evaluated in vitro for effectiveness in protecting aptamers against enzymatic degradation through stability studies of corresponding prodrug complexes and control (unbound) aptamers. Synthetic receptors affording protection are then tested for their ability to efficiently deliver aptamers to therapeutic targets in vitro. Prodrug complexes comprising each selected aptamer specifically bound to each selected synthetic receptor are incubated alone and in combination with isolated preparations of HIV reverse transcriptase, and the rate, degree and duration of enzyme inhibition are compared with control conditions (enzyme alone, enzyme plus aptamer(s), enzyme plus synthetic receptor(s)). Selected prodrug complexes and combinations are then tested for safety and efficacy in preclinical and clinical studies.

Example 3

Prodrug Complex Comprising Antiplatelet Formulations as Antithrombotics

Vascular thrombotic events associated with myocardial infarction, percutaneous transluminal coronary angioplasty (PTCA), stroke, peripheral arterial occlusion and venous hromboembolism, among other conditions, cause significant orbidity and mortality. Intense antithrombin and antiplatelet rug development efforts are underway to reduce the incidence of thrombotic events. Because rethrombosis occurs in 15% to 35% of treated patients, a major drug development focus for the treatment of acute myocardial infarction is maintaining vessel patency following thrombolytic therapy. Another major focus is reducing the incidence of restenosis following PTCA procedures from the historical rate of about 30%. Other important applications for antithrombin and antiplatelet agents include chronic maintenance of vessel patency following coronary artery bypass surgery and post-thromboembolitic stroke.

Pharmacologic approaches to thrombosis include prostaglandins, calcium channel blockers and anti-fibrinogen agents; antagonists of platelet activating factor and glycoprotein (Gp) Ib, IIb and IIIa receptors; ticlopidine, which alters GP IIb/IIIa receptor expression; and inhibitors of cyclooxygenase, thrombin, phosphodiesterase and thromboxane synthetase. Significant evidence indicates that fibrinogen binding to the platelet Gp IIb/IIIa (adhesion) receptor is the final common pathway of platelet aggregation, suggesting the utility of effective Gp IIb/IIa receptor antagonists. CENTORX (Centocor; Malvern, Pa.) is a chimeric anti-7E3 Fab fragment with Gp IIb/IIIa receptor specificity. RGD and RGDS peptides bind the active site of the Gp IIb/IIIa receptor through the adhesive protein recognition sequences Arg-Gly-Asp and Arg-Gly-Asp-Ser, respectively, which are essential for fibrinogen-receptor interaction. However, the clinical and commercial potential of such antibodies and peptides as antithrombotics is limited by their unacceptably short half-lives. Platelet Gp Ib receptors interact with von Willebrand factor associated with damaged vascular endothelium to initiate platelet adhesion. Adhesion is followed by platelet aggregation which, in turn, leads to thrombus formation. Gp Ib receptor antagonists may therefore interrupt thrombus formation at an earlier point in the pathologic cascade than Gp IIb/IIa receptor antagonists.

Administration of a drug specifically bound to an immobilized synthetic receptor as in the present invention can increase the circulating half-life and therapeutic efficacy of the drug, as exhibited by enhanced antithrombotic performance of a platelet receptor antagonist. For example, a therapeutic composition comprising a Gp IIb/IIIa receptor antagonist (e.g., RGDS peptide SK&F 106760 (SmithKline Beecham; Philadelphia, Pa.), Britistatin or Echistatin (both of Merck; Rahway, N.J.)) specifically bound to selected synthetic receptors operatively attached to red blood cells obtained by autologous or heterologous donation. Synthetic receptors are selected for specific binding to platelet Gp IIb/IIIa receptor antagonists in accordance with methods described in Examples 1 and 2. Selected synthetic receptors are attached to red cell membranes either covalently (e.g., by chemical conjugation) or by noncovalent partitioning into the lipid bilayer following conjugation to a lipophilic carrier (e.g., a Zyn-Linker, glycolipid or synthetic phospholipid). Red cell-prodrug complexes are then prepared by addition of the Gp IIb/IIIa receptor antagonist to synthetic receptor-modified red cells. Prodrug-modified red cells, stored at 2–8° C. until use, are administered perioperatively by intravenous infusion.

Multi-prodrug complexes such as these are designed for therapeutic applications requiring prolonged therapeutic action at extracellular or external membrane receptors. Preferred embodiments favor distribution and retention of systemically administered drugs within particular physiologic compartments, such as the circulation or lymphatic system. Representative applications include, but are not limited to, cardiovascular, respiratory, endocrine, immune, hematologic and anti-infective therapeutics.

Example 4

Topical Treatment of Psoriasis Using Soluble Interleukin Receptors Specifically Bound to Immobilized Synthetic Receptors Psoriasis is generally classified as an autoimmune inflammatory disorder. Although the etiology and pathogenesis have not been fully elucidated, interactions among genetic, immunologic and environmental factors appear to be important. First-line therapy consists of lubricants, keratolytics and topical corticosteroids. Topical steroids are the primary treatment for mild psoriasis, but adverse effects are caused by diffusion of drug into the circulation. Severe psoriasis is not well managed by topical steroids which may induce tolerance, toxicity and side effects with chronic use.

Interleukins (IL) have been implicated in the pathogenesis of psoriasis. IL-8, released during both acute and chronic phases of inflammatory diseases, causes both accumulation and activation of neutrophils which, in turn, produce cytotoxic agents. IL-1, IL-4 and IL-7 have also been implicated in immune-mediated inflammatory diseases. Several companies (e.g., Repligen (Cambridge, Mass.), Immunex (Seattle, Wash.)) are developing soluble receptors of interleukins, particularly IL-1 and IL-8, as a means of scavenging released cytokines and interrupting the inflammatory cascade.

The prodrug complexes of the present invention provide a means of retaining topically administered anti-cytokine agents (e.g., soluble IL receptors or receptor antagonists) in prodrug form at sites of inflammation. Dissociation of active drug in proportion to local cytokine levels provides for target-dependent drug delivery.

For example, a prodrug complex comprising a soluble interleukin receptor (e.g., IL-1 receptor, IL-8 receptor) specifically bound to a selected synthetic receptor operatively attached to a liposome, lipid complex or lipophilic matrix in a topical cream, ointment or gel can be formulated. Because the synthetic receptor is selected for its ability to specifically bind a pathophysiologic receptor, it is considered a ligand or interleukin mimetic.

Selected synthetic receptors are attached to liposomes, lipid complexes or lipid matrices either by direct covalent attachment or by noncovalent association following conjugation to a lipophilic carrier. Synthetic receptor-modified liposomes, lipid complexes or lipid matrices are converted to immobilized prodrug complexes by incubation with drug (e.g., IL-1 receptor, IL-8 receptor). Immobilized prodrug complexes are then incorporated into a penetrating cream, gel or ointment which is applied topically to psoriatic lesions. Locally released interleukins (having a higher affinity than immobilized synthetic receptors for soluble IL receptors) compete with immobilized synthetic receptors (prodrug complexes) for specifically bound soluble IL receptors. Released interleukins are scavenged by soluble IL receptors which dissociate from immobilized prodrug complexes, thereby preventing cytokine-mediated recruitment and activation of neutrophils and interrupting the downstream inflammatory cascade.

While treatment of psoriasis is exemplified, as will be obvious to one of skill in the art upon this disclosure, these prodrug complexes comprising a drug which is a soluble receptor specifically bound to a synthetic receptor which is a ligand are useful in treating a number of different anatomically localized conditions. Preferably, complexes of this type are used for anatomically confined conditions involving locally proliferating, released or recruited therapeutic targets. Representative applications include localized infections, inflammatory, allergic and immune disorders.

What is claimed is:

1. A method of producing a prodrug complex for administration to an organism comprising:
   (a) identifying a drug;
   (b) selecting a synthetic receptor that specifically binds the drug via a saturable, noncovalent interaction between the drug and the synthetic receptor that can be competitively inhibited by structural analogs of the drug, said synthetic receptor being selected from the group consisting of antibodies, antibody fragments, oligonucleotides and oligosaccharides; and (c) specifically binding the identified drug to the selected synthetic receptor to form a prodrug complex consisting essentially of the identified drug specifically bound to the selected synthetic receptor.

2. The method of claim 1 further comprising attaching the prodrug complex to a biologic or biocompatible structure.

3. A method of producing a multi-prodrug complex for administration to an organism, said multi-prodrug complex comprising first and second prodrug complexes, wherein the first prodrug complex is produced in accordance with the method of claim 1 and the second prodrug complex comprises a drug bound to a synthetic receptor.

4. A prodrug complex for administration to an organism, said prodrug complex being produced in accordance with the method of claim 1.

5. A drug delivery system comprising the prodrug complex of claim 4 attached to a biologic or biocompatible structure selected from the group consisting of molecules, molecular complexes, microstructures, cells, vesicles, microparticles, polymers, gels, matrices, blood forming elements, reticuloendothelial cells, liposomes, microspheres, nanostructures, biopolymers, multimolecular complexes, cell membranes, implants and prosthetic devices.

6. A multi-prodrug complex for administration to an organism, said multi-prodrug complex comprising first and second prodrug complexes, wherein the first prodrug complex is produced in accordance with the method of claim 1 and the second prodrug complex comprises a drug bound to a synthetic receptor.

7. A drug delivery system comprising the multi-prodrug complex of claim 6 attached to a biologic or biocompatible structure selected from the group consisting of molecules, molecular complexes, microstructures, cells, vesicles, microparticles, polymers, gels, matrices, blood forming elements, reticuloendothelial cells, liposomes, microspheres, nanostructures, biopolymers, multimolecular complexes, cell membranes, implants and prosthetic devices.

* * * * *